(12) United States Patent
Taylor et al.

(10) Patent No.: US 10,278,781 B2
(45) Date of Patent: *May 7, 2019

(54) TOOL EXCHANGE INTERFACE AND CONTROL ALGORITHM FOR COOPERATIVE SURGICAL ROBOTS

(71) Applicant: The Johns Hopkins University, Baltimore, MD (US)

(72) Inventors: Russell H. Taylor, Severna Park, MD (US); Marcin Arkadiusz Balicki, Baltimore, MD (US); James Tahara Handa, Baltimore, MD (US)

(73) Assignee: The John Hopkins University, Baltimore, MD (US)

( * ) Notice: Subject to any disclaimer, the term of this patent is extended or adjusted under 35 U.S.C. 154(b) by 75 days.

This patent is subject to a terminal disclaimer.

(21) Appl. No.: 15/383,931

(22) Filed: Dec. 19, 2016

(65) Prior Publication Data

US 2017/0156805 A1 Jun. 8, 2017

Related U.S. Application Data

(63) Continuation of application No. 13/813,717, filed as application No. PCT/US2011/046268 on Aug. 2, 2011, now Pat. No. 9,554,864.

(Continued)

(51) Int. Cl.
*A61B 34/30* (2016.01)
*A61B 34/32* (2016.01)
(Continued)

(52) U.S. Cl.
CPC .............. *A61B 34/32* (2016.02); *A61B 34/30* (2016.02); *A61B 90/06* (2016.02);
(Continued)

(58) Field of Classification Search
CPC ......... A61B 34/30; A61B 34/32; A61B 90/06; A61B 2017/00477; A61B 2090/064;
(Continued)

(56) References Cited

U.S. PATENT DOCUMENTS 4,500,065 A 2/1985 Hennekes et al.
5,695,500 A 12/1997 Taylor et al.
(Continued)

FOREIGN PATENT DOCUMENTS

CN 101242788 A 8/2008
CN 101340850 A 1/2009
(Continued)

OTHER PUBLICATIONS

Balicki et al., "Single fiber optical coherence tomography microsurgical instruments for computer and robot-assisted retinal surgery," *Proceedings of the MICCAI Conference*, London, 108-115 (2009).
(Continued)

*Primary Examiner* — Nathan J Jenness
(74) *Attorney, Agent, or Firm* — Venable LLP; Henry J. Daley

(57) ABSTRACT

A system and method for tool exchange during surgery for cooperatively controlled robots comprises a tool holder for receiving a surgical tool adapted to be held by a robot and a surgeon, a tool holding element for constraining downward motion of the tool while allowing low force removal of the surgical tool from the holder, a first sensor for detecting if the surgical tool is docked within the tool holder, and a selector for automatically selecting different movements or actions of the tool holder to be performed based upon information detected by the first sensor. The system and method of the present invention provides an advantage to an often slow moving cooperative robot, by increasing the
(Continued)

speed by which the tool holder may move in the direction away from the patient.

19 Claims, 2 Drawing Sheets

Related U.S. Application Data

(60) Provisional application No. 61/370,027, filed on Aug. 2, 2010.

(51) Int. Cl.
*B25J 15/04* (2006.01)
*A61B 90/00* (2016.01)
*A61B 17/00* (2006.01)

(52) U.S. Cl.
CPC . *B25J 15/0466* (2013.01); *A61B 2017/00477* (2013.01); *A61B 2090/064* (2016.02); *A61B 2090/065* (2016.02); *A61B 2090/0811* (2016.02)

(58) Field of Classification Search
CPC ....... A61B 2090/065; A61B 2090/0811; B25J 15/0466
USPC .................................................... 606/1, 130
See application file for complete search history.

(56) References Cited

U.S. PATENT DOCUMENTS

| | | |
|---|---|---|
| 6,079,681 A | 6/2000 | Stern et al. |
| 6,840,895 B2 | 1/2005 | Perry et al. |
| 8,793,887 B2 | 8/2014 | Lange et al. |
| 2002/0010479 A1* | 1/2002 | Skakoon ................ A61B 34/20 606/130 |
| 2002/0032452 A1 | 3/2002 | Tierney et al. |
| 2004/0106916 A1 | 6/2004 | Quaid et al. |
| 2004/0243147 A1 | 12/2004 | Lipow |
| 2005/0149003 A1 | 7/2005 | Tierney et al. |
| 2006/0161136 A1 | 7/2006 | Anderson et al. |
| 2006/0195070 A1 | 8/2006 | Hagn |
| 2010/0160930 A1 | 6/2010 | Green et al. |

FOREIGN PATENT DOCUMENTS

| | | |
|---|---|---|
| JP | 2003-093403 A | 4/2003 |
| WO | WO-03/013783 A1 | 2/2003 |
| WO | WO-2009/140688 A2 | 11/2009 |

OTHER PUBLICATIONS

Mitchell et al.: Development and application of a new steady-hand manipulator for retinal surgery. In: ICRA, Rome, Italy (2007) 623-629.

Uneri et al., "New steady-hand EyeRobot with micro-force sensing for vitreoretinal surgery," In: Proceedings of IEEE BioRob, pp. 814-819, Sep. 26-29, 2010.

\* cited by examiner

TOOL EXCHANGE INTERFACE AND CONTROL ALGORITHM FOR COOPERATIVE SURGICAL ROBOTS

REFERENCE TO RELATED APPLICATIONS

This application is a Continuation of U.S. patent application Ser. No. 13/813,717, filed Oct. 21, 2013, which is a 35 U.S.C. § 371 U.S. national entry of International Application PCT/US2011/046268 having an international filing date of Aug. 2, 2011, which claims the benefit of U.S. Provisional Patent Application No. 61/370,027, filed on Aug. 2, 2010, the content of each of the aforementioned applications is herein incorporated by reference in their entireties.

STATEMENT OF GOVERNMENTAL INTEREST

This invention was made with government support under grant no. EB007969 awarded by the National Institutes of Health (NIH) and EEC9731478 awarded by the National Science Foundation (NSF). The government has certain rights in the invention.

FIELD OF THE INVENTION

The present invention pertains to a tool exchange interface for surgical robots. More particularly, the present invention pertains to a tool exchange interface and control algorithm for cooperative surgical robots.

BACKGROUND OF THE INVENTION

In the "hands-on" cooperative robot control paradigm, both the operator and the robot hold the tool while the forces exerted by the operator on the tool are sensed with a force/torque sensor and the robot moves to minimize these forces, effectively rendering the operator's desired motion. For surgical applications, quick tool changes are desirable and often required for timing and safety reasons. Specifically, unintended patient movement requires an immediate compensatory repositioning of the instrument to avoid tissue injury.

A quick tool exchange mechanism is desirable for a surgical system based on cooperatively controlled robot where frequent insertion and removal of surgical instruments is required, e.g., Vitreoretinal surgery. For safety reasons, this tool interface should also provide a very quick and robust instrument removal from the surgical site that is not dependent on a functioning robot. While engaged, this mechanism should not impede the function of the robot or the ability of the surgeon to perform desired tasks.

One approach to this problem is to use a simple d-tenting mechanism in which a small spring-loaded ball or pin in the tool holder engages a socket or groove on the tool shaft to hold the tool in place unless a sufficiently large force is exerted to disengage the tool. Another approach is to use a magnet. One challenge with these approaches is holding the tool firmly enough to permit the operator to guide the tool without unintended break-away while also ensuring that the required release force is not so large that the tool cannot be removed very quickly and safely if the need arises. This challenge is especially crucial in applications such as retinal microsurgery, where the forces are extremely delicate and the need for very quick, non-disruptive tool withdrawal is great.

Accordingly, there is a need in the art for a system and method for assisting with tool exchange during surgery.

SUMMARY

According to a first aspect of the present invention, a system for tool exchange during surgery for cooperatively controlled robots comprises a tool holder for receiving a surgical tool adapted to be held by a robot and a surgeon, a tool holding element for constraining downward motion of the tool while allowing low force removal of the surgical tool from the holder, a first sensor for detecting if the surgical tool is docked within the tool holder, and a selector for automatically selecting different movements or actions of the tool holder to be performed based upon information detected by the first sensor.

According to a second aspect of the present invention, a method for tool exchange for cooperatively controlled robots comprises providing a tool holder for receiving a surgical tool adapted to be held by a robot and a surgeon, constraining downward motion of the surgical tool while allowing low force removal of the tool from the holder, detecting if the surgical tool is docked within the tool holder, and automatically selecting different movements or actions of the tool holder to be performed based upon information detected.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION OF THE PREFERRED EMBODIMENTS

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention pertains to a system and method for tool exchange of a surgical tool during cooperatively controlled robots. An exemplary embodiment of the invention provides for use of the system and method in cooperatively controlled hand-over-hand systems is described in "Development and Application of a New Steady-Hand Manipulator for Retinal Surgery", Mitchell et al., IEEE ICRA, pp. 623-629 (2007) and in "New Steady-Hand Eye Robot with Microforce Sensing for Vitreoretinal Surgery Research", A. Uneri, M. Balicki, James Handa, Peter Gehlbach, R. Taylor, and I. Iordachita, International Conference on Biomedical Robotics and Biomechatronics (BIOROB), Tokyo, Sep. 26-29, 2010. pp. 814-819, the entire contents of which are incorporated by reference herein. In steady-hand control, the surgeon and robot both hold the surgical tool. The robot senses forces exerted by the surgeon on the tool handle, and moves to comply, filtering out any tremor. While a specific cooperative control system is described in connection with the above publication, it should be understood that the system and method of the present invention may also be applicable to other cooperatively controlled systems.

Figure 1A:
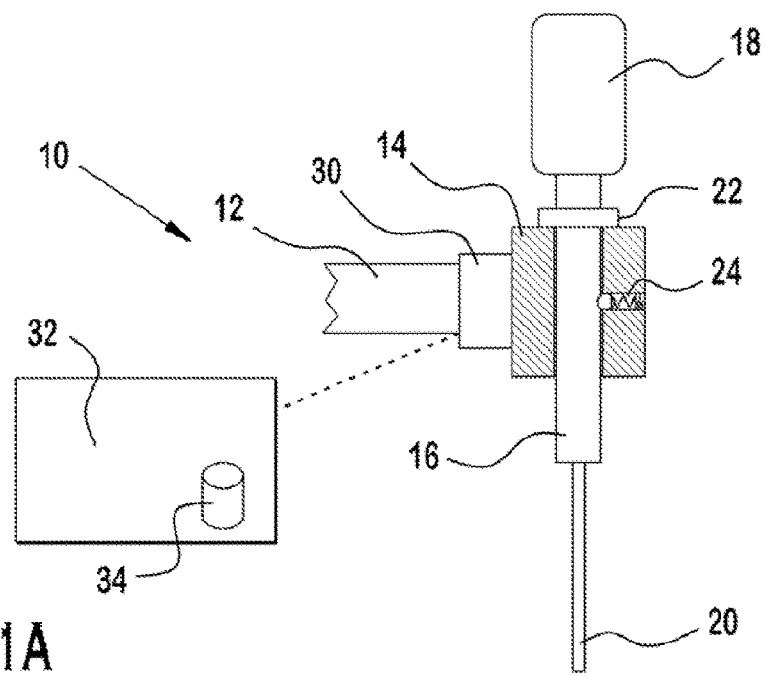
FIG. 1A illustrates a side elevated view of an exemplary product according to the features of the present invention.
Figure 1B:
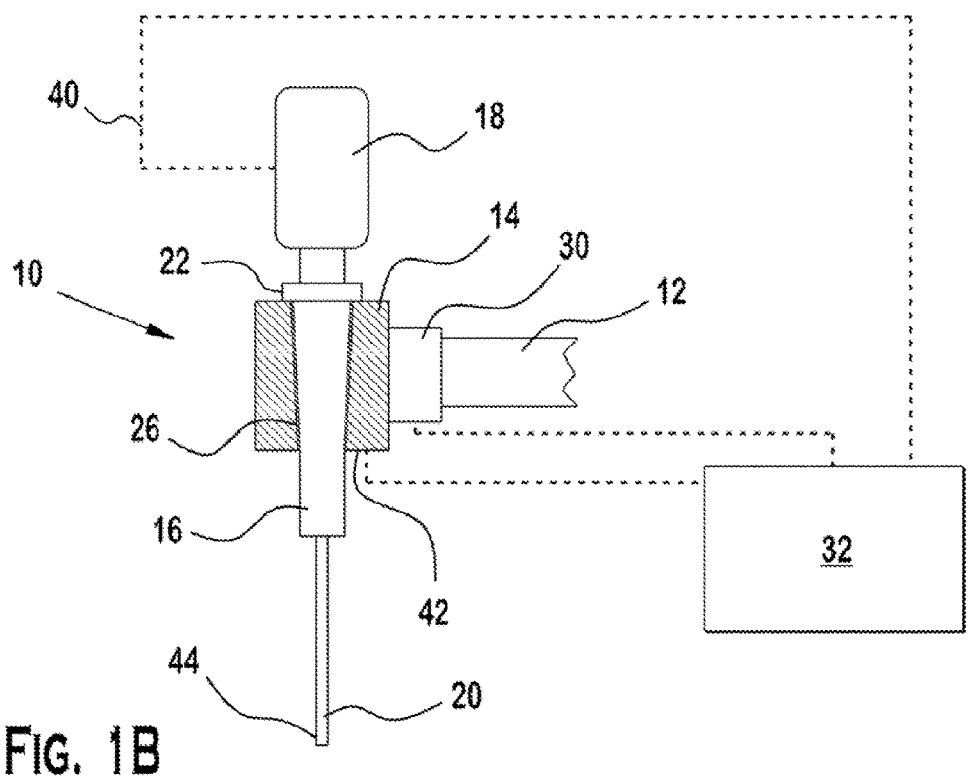
FIG. 1B illustrates a side elevated view of an exemplary product according to the features of the present invention.
Figure 2A:
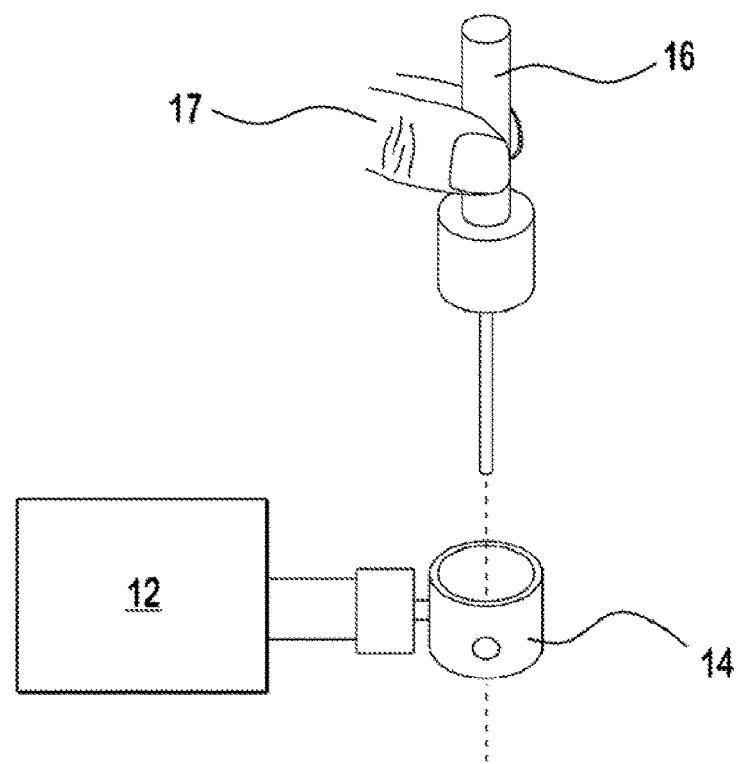
FIG. 2A illustrates a perspective view of an exemplary product according to the features of the present invention.
Figure 2B:
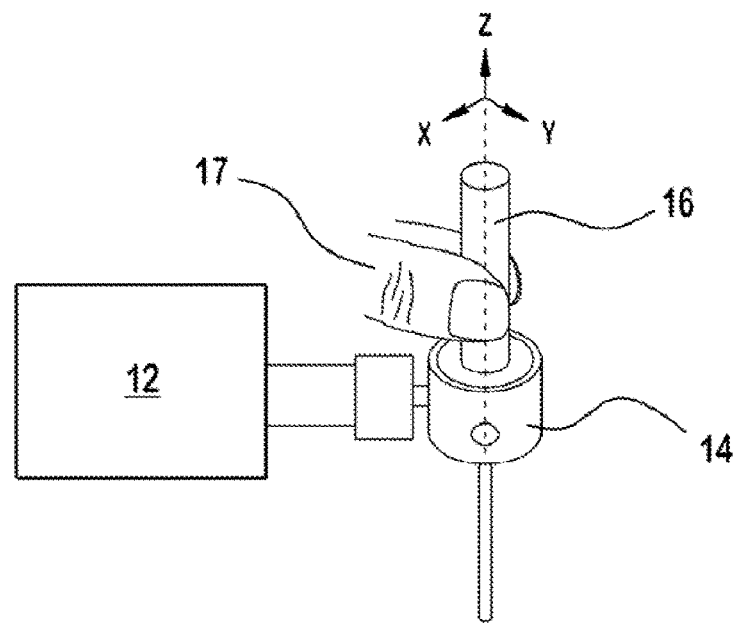
FIG. 2B illustrates a perspective view of an exemplary product according to the features of the present invention.

With reference to FIGS. 1A and 1B and FIGS. 2A and 2B, an exemplary embodiment of a cooperatively controlled surgical system to be used in connection with the present invention is shown. The system 10 may be used in microsurgery of organs, for example, hollow organs, such as the human eye. However, other applications are possible and within the scope of the invention. As shown in FIGS. 1A, 1B, 2A, and 2B, a robot 12 includes tool holder 14 for receiving a surgical tool 16 to be held by both the robot 12 and a surgeon 17 (FIGS. 2A and 2B). Preferably, the surgeon 17 holds the surgical tool 16 at a tool handle 18, and cooperatively directs the surgical tool 16 with the robot 12 to perform surgery of a region of interest with a tool tip 20.

With reference to FIG. 1A, a tool holding element 24 is provided for constraining downward motion of the surgical tool 16 while allowing low force removal of the surgical tool 16 from the tool holder 14. In the exemplary embodiment in FIG. 1A, the tool holding element 24 is a d-tenting mechanism in which a small spring-loaded ball or pin in the tool holder 14 engages a socket or groove on the tool shaft to hold the surgical tool in place unless a sufficiently large force is exerted to disengage the surgical tool 16. A flange 22 on the surgical tool 16 may also be used to restrict downward motion of the tool.

With reference to FIG. 1B, an alternative embodiment of the system 10 includes a different type of tool holding element 26. In particular, the tool holding element 26 may be one or more tapered surfaces along either the tool shaft itself, or the internal channel of the tool holder. For example, the tool holder channel may be a circular cross section or some other cross section constraining the axial rotation of the tool relative to the tool holder. Other examples of tool holding elements include magnets, vacuum chucks, or any other mechanical or electromechanical devices to keep the surgical tool in place, while allowing low breakaway forces. The tool holding element should be sufficiently strong so that the tool is held firmly enough to allow the operator to guide the tool without unintended breakaway while also ensuring that the required release force not be so large that the tool cannot be removed safely and quickly.

According to the features of the present invention, a first aspect of the invention is to provide feedback information regarding whether a tool is engaged within the tool holder. That is, a first sensor may be provided for detecting if the surgical tool is docked within the tool holder 14. For example, with reference to FIG. 1B, a sensor 42 may be positioned in the tool holder 14 to detect the position of the surgical tool 16 within the tool holder 14. Sensor 42 may include, but is not limited to, a proximity sensor (IR, Hall Effect) imbedded in the tool holder. As shown in FIG. 1B, the sensor 42 is preferably disposed at a distal end of the tool. Because of the location of the sensor 42 at the distal end of the tool holder 14, the sensor 42 is operated when the tool is engaged in the holder.

In addition, other sensors may be used to detect if the surgical tool 16 is docked or engaged in the tool holder 14, including but not limited to, a contact sensor, a toggle switch or pressure sensor, a beam-break type of optical sensor, direct contact force sensor, and a displacement potentiometer. Further, a multiplicity of sensors may be used in a redundant manner to detect whether the tool is fully engaged with the tool holder.

According to the features of the present invention, a selector is provided that automatically selects different movements or actions of the tool holder to be performed based upon information detected by the sensor, e.g., whether the tool is engaged in the tool holder, which will be described in more detail below. For example, when a sensor detects that the tool is not fully engaged within the tool holder, the robot may actively move along the tool axis to restore that connection based on one or more contact sensing methods. If the tool is fully engaged in the tool holder, the robot moves to respond to motions commanded by the surgeon user, for example by exerting forces on the handle of the tool.

According to another aspect of the present invention, the forces between a surgeon and tool may also be detected. For example, a number of sensors known in the art may be used to detect whether the tool 16 is held by the surgeon. For example, and with reference to FIG. 1B, a sensor 40 may be disposed on the tool handle. Sensor 40 may include but is not limited to micro-switches, capacitive sensors, optical sensors, force sensors, or pressure sensors on the tool handle 18. The robot can be programmed so that if the operator releases the tool handle, the robot will automatically retract the tool by a predetermined amount or a predetermined distance or to perform some other "disengaged" behavior. Similarly, when the tool is held firmly in the tool holder, the breakaway force is high. A rise in the axial force in the direction of tool retraction up to some known break-away force, followed by a sudden drop to zero force is characteristic of tool breakaway. When handle forces fall below a desired threshold or there is no handle contact or until the system otherwise detects that the tool is no longer engaged in the tool holder, the robot may move along the tool axis in the designated direction, e.g., back away from the risky area (or performs any other predefined disengaged behavior). This backing away motion may continue for some pre-determined threshold distance or until re-engagement of the tool with the tool holder is detected. The robot may be prevented from moving in a particular direction, such as along the tool axis direction toward the patient, until the tool is fully re-engaged in the tool holder. In the case where a handle force sensor is used to detect re-engagement of the tool with the tool holder, there may be a characteristic time sequence of force values used to detect re-engagement. For example, if a D-tenting mechanism is used to hold the tool in the tool-holder, the axial force along the tool will typically rise to a characteristic value and then decrease. Subsequently, the surgeon can be instructed to pull the tool gently along the tool axis in the retraction direction, though not hard enough to disengage the tool. If the tool is properly engaged, these forces will be detected by the force sensor.

With reference to FIG. 1A, the system may also include a force sensor 30 which provides forces for the force control laws. The force sensor 30 may also detect forces exerted by the surgeon on the surgical tool when a surgical tool 16 is engaged within the tool holder 14. As shown in FIG. 1A, force sensor 30 may be located between the tool holder 14 and the robot 12. Forces exerted by the surgeon on the tool handle are transmitted through the tool holder 14 to the force sensor 30. If the tool is not fully engaged in tool holder 14, then no forces in the downward z-direction along the tool shaft will be measured, but it may be possible to measure lateral forces in the other directions. In other embodiments, the force sensor 30 may be mounted in the handle 18 of the surgical tool or elsewhere.

The force sensor 30 may also be used to detect if the surgical tool 16 is within the tool holder 14, or if the surgical tool 16 is held by the surgeon. That is, a single sensor 30 can sense (1) whether the surgical tool is within the tool holder; and (2) whether the surgical tool is held by the surgeon. However, two separate sensors may also be used. Alternatively, an existing force/torque sensor 30 may be used to sense when the tool is engaged in the tool holder 14 in the downward z-direction. If no downward force is detected by the sensor 30, the surgical tool 16 can be considered disengaged from the tool holder. If the only force detected by the sensor 30 is a downward force equal to the weight of the tool, then the tool may be considered engaged with the tool holder 14, but disengaged from the surgeon.

It should be understood that any number of sensors (including just a single sensor) may be used to detect whether the tool is engaged in the tool holder. The information detected can then be used to determine the appropriate movement of the robot. The choice of sensors and location of sensors depends upon application and design preference.

With reference FIGS. 1A and 1B, the detected values from the applied sensor(s) is/are sent to a data processor 32 for necessary processing according to features of the present invention. The data processor 32 includes a memory device 34 having a program with machine readable instructions for performing the necessary algorithms for assisting with tool exchange according to features of the present invention. The data processor 32 may be a stand-alone computer system, or could be incorporated into existing software. For example, in the context of robotic surgery, the data processor 32 could be incorporated into existing software for the cooperative surgical systems.

The data processor 32 includes a program that automatically selects different movements or actions of the tool holder to be performed based upon information detected by the sensors. For example, with reference to FIG. 1A, if a sensor senses that the surgical tool 16 is docked in the tool holder 14 and senses a force that is consistent with removal of the surgical tool, the tool holder 14 is moved in a direction of the force applied along a tool axis to reengage the surgical tool 16. Preferably, the tool holder is moved with an asymmetric gain in velocity. Likewise, with reference to FIG. 1B, if the switch 40 is disengaged indicating non-use by the surgeon, the tool may be released from the tool holder 14 when the condition of non-use is sensed for a predetermined period of time.

With reference to FIG. 1B, the surgical tool 16 may also include a proximity sensor 44 disposed at its tip for sensing tool to tissue distance. However, it should be understood that the proximity sensor 44 may be at other different locations, and need not be at the tool tip. Preferably, the tool to tissue distance is fed back to the data processor 32, and an appropriate action or movement may be performed in response to the detected value. For example, if the tool to tissue distance is a predetermined level indicative of non-use, the tool holder 14 may be moved to a desired standoff distance. See, e.g.,] M. Balicki, J.-H. Han, I. Iordachita, P. Gehlbach, J. Handa, R. H. Taylor, and J. Kang, "Single Fiber Optical Coherence Tomography Microsurgical Instruments for Computer and Robot-Assisted Retinal Surgery", in Medical Image Computing and Computer Assisted Surgery (MICCAI 2009), London, Sep. 20-24, 2009. pp. 108-115. PMID: 20425977, the entire contents of which are incorporated by reference herein.

Importantly, the system and method of the present invention provides an advantage to an often slow moving cooperative robot, by increasing the speed by which the tool holder may move in the direction away from the patient.

EXAMPLE

The following Example has been included to provide guidance to one of ordinary skill in the art for practicing representative embodiments of the presently disclosed subject matter. In light of the present disclosure and the general level of skill in the art, those of skill can appreciate that the following Example is intended to be exemplary only and that numerous changes, modifications, and alterations can be employed without departing from the scope of the presently disclosed subject matter. The following Example is offered by way of illustration and not by way of limitation.

A variety of algorithms can be used to automatically select different movements or actions of the tool holder to be performed based upon information detected from a particular sensor. For example, if a sensor detects that the tool is disengaged then $$\dot{x}_h = \alpha F_h \text{ but with } \dot{x}_{hz} = f(s,t)$$

Otherwise $$\dot{x}_h = \alpha F_h$$

$F_h$—Force/Torques resolved at the handle contact position $F_{hZ}$—Force in handle coordinates along the Z axis $\dot{x}_h$—Desired handle velocity in handle coordinates $\alpha$—Constant that translates handle input force to handle velocity.

$f(s,t)$—function that generates a desired handle response based on sensor input and time.

Some examples for $f(s,t)$ are provided below. For example, when the tool is disengaged, set constant velocity: $f(s,t)=\beta$ for a short period t (after motion stops), so that the tool has moved up by a fixed amount bt. In addition, when using a proximity sensor sensing the distance s of the tool from the patient's anatomy, set $f(s,t)=g(s_{standoff}-s)$ or $f(s,t)=g$ to achieve a standoff distance $s_{standoff}$. If there is a displacement or proximity sensor sensing a distance $d_{tool}$ of the tool from the engaged position in the tool holder, set $f(s,t)=gd_{tool}$ to cause the tool holder to move up to fully seat the tool.

The tool may be considered disengaged if $F_{hZ}=F_{thresh}$, where $F_{thresh}$ is some threshold force (negative for pushing down), and any of the above methods may be used to implement the desired "disengaged" behavior. Alternatively, the robot may be programmed to move to maintain a minimum desired tool-to-holder contact force. For example, $\dot{x}_{hz}=a(F_{hZ}-F_{thresh})$ would cause the tool holder to creep slowly up if the tool handle is released.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. A system for tool exchange or quick release during surgery for cooperatively controlled robots, comprising:
   a tool holder configured to receive a surgical tool, the surgical tool being adapted to be held a surgeon, the tool holder being connected to a robot;
   a tool holding element configured to constrain downward motion of the tool relative to the tool holder while allowing removal of the surgical tool from the tool holder;
   a first sensor configured to detect if the surgical tool is docked within the tool holder; and
   a selector configured to automatically select different movements or actions of the tool holder to be performed based upon information detected by the first sensor,
   wherein the selector is configured to control the tool holder to move away from a surgical area when the first sensor detects that the surgical tool is not fully engaged or docked within the tool holder, or to move in a direction of a force applied to the surgical tool to reengage the surgical tool when the first sensor detects that the surgical tool is disengaged from the tool holder.

2. The system of claim 1, further comprising a second sensor configured to detect forces exerted by the surgeon on the surgical tool or robot.

3. The system of claim 2, wherein the second sensor is configured to detect the forces exerted by the surgeon on the surgical tool or robot and to detect when the surgical tool is not fully engaged in the tool holder based on the detected forces, wherein the second sensor is configured to communicate with the selector to control the tool holder to automatically retract when the surgical tool is not fully engaged in the tool holder.

4. The system of claim 2, wherein the first sensor comprises an optical sensor, said optical sensor being a beam break type of sensor for determining the location of the tool inside the tool holder.

5. The system of claim 1, wherein the first sensor is a proximity sensor embedded within the tool holder configured to sense a location of the tool with respect to the tool holder.

6. The system of claim 5, wherein the proximity sensor is disposed at a distal end of the tool holder.

7. The system of claim 1, wherein the first sensor comprises a contact sensor.

8. The system of claim 7, wherein the contact sensor comprises a toggle switch or a pressure sensor.

9. The system of claim 1, wherein the first sensor comprises a displacement potentiometer.

10. The system of claim 1, wherein the tool holder is configured to move in a direction of the force applied along a tool axis to reengage the surgical tool when a predetermined level of force consistent with removal of the surgical tool is sensed.

11. The system of claim 10, wherein the tool holder is configured to move with an asymmetric gain in velocity.

12. The system of claim 1, wherein the tool holder is configured to move based upon whether the tool is engaged or not.

13. The system of claim 1, wherein the tool holding element comprises a flange configured to receive the surgical tool.

14. The system of claim 1, wherein the tool holding element includes cooperative tapered surfaces configured to come in contact with surfaces of said surgical tool.

15. The system of claim 1, further comprising a sensor configured to detect tool to tissue distance, wherein said tool holder is configured to move to a desired standoff distance when the detected tool to tissue distance reaches a predetermined level.

16. A method for tool exchange or quick release for cooperatively controlled robots, comprising:
   providing a surgical tool adapted to be held by a surgeon;
   providing a tool holder for receiving the surgical tool, the tool holder being connected to a robot;
   constraining downward motion of the surgical tool with the tool holder while allowing removal of the surgical tool from the tool holder;
   detecting by a first sensor if the surgical tool is docked within the tool holder;
   automatically selecting different movements or actions of the tool holder to be performed based upon information detected;
   controlling the tool holder to move away from a surgical area when the first sensor detects that the surgical tool is not fully engaged or docked within the tool holder, or to move in a direction of a force applied to the surgical tool to reengage the surgical tool when the first sensor detects that the surgical tool is disengaged from the tool holder.

17. The method of claim 16, further comprising moving the tool holder in a direction of the force applied along a tool axis to re-engage the surgical tool when a predetermined level of force consistent with removal of the tool is sensed.

18. The method of claim 17, further comprising moving the tool holder with an asymmetric gain in velocity.

19. The method of claim 16, further comprising releasing the tool from the tool holder when the surgeon is not grasping the surgical tool.

* * * * *